United States Patent [19]
Janick et al.

[11] 4,291,498
[45] Sep. 29, 1981

[54] METHOD FOR PRODUCTION OF MATURE ASEXUAL CACAO EMBRYOS, AND PRODUCT THEREOF

[75] Inventors: Jules Janick; Paul M. Hasegawa, both of West Lafayette, Ind.; Valerie C. Pence, Gainesville, Fla.

[73] Assignee: Purdue Research Foundation, West Lafayette, Ind.

[21] Appl. No.: 131,883

[22] Filed: Mar. 20, 1980

[51] Int. Cl.³ .............................................. A01G 1/00
[52] U.S. Cl. ...................................................... 47/58
[58] Field of Search ........................................... 47/58

[56] References Cited
U.S. PATENT DOCUMENTS
4,204,366  5/1980  Janick et al. ............................. 47/58

Primary Examiner—Robert E. Bagwill
Attorney, Agent, or Firm—John R. Nesbitt

[57] ABSTRACT

A method for growth, development and maturation of cacao embryos from the precursor stage disclosed in U.S. application Ser. No. 951,267, and product of such method of production.

12 Claims, 2 Drawing Figures

METHOD FOR PRODUCTION OF MATURE ASEXUAL CACAO EMBRYOS, AND PRODUCT THEREOF

FIELD OF THE INVENTION

This invention relates to a method for in vitro enhancement and maturation of embryos of cacao, and the product of such method.

BACKGROUND OF THE INVENTION

The general state-of-the-art is described in U.S. patent application Ser. No. 951,267, filed Oct. 13, 1978, (and now U.S. Pat. No. 4,204,366) Jules Janick and Valerie C. Pence, inventors, entitled "Method of Non-Agricultural Production of Cotyledons," and a division thereof, filed Jan. 11, 1980, application Ser. No. 111,960 entitled "A Plant Tissue Produced by Non-Agricultural Proliferation of Cacao Cotyledons."

The improvement here proposed is a definition of the proper conditions under which the cacao cotyledons produced by the method disclosed in the aforesaid patent applications may be produced and matured to a cocoa butter-like product.

SUMMARY OF THE INVENTION

The in vitro production of cotyledons of the cacao plant (*Theobroma cacao L.*) for the production of useful products such as cocoa solids and cocoa butter involves at least four steps, namely, initiation of asexual embryos; proliferation of asexual embryos; growth, development and maturation of asexual embryos; and the harvest of cotyledons.

This invention teaches the proper growth media for carrying out said steps.

Media additives and environmental and developmental conditions are described that induce and direct the: (1) initiation of asexual embryos from zygotic embryos; (2) proliferation of asexual embryos from embryonic tissues; (3) development of asexual embryos to maturity from embryonic tissues; (4) growth of asexual embryos without precocious germination; (5) development of anthocyanin in asexual embryos; and (6) the development of cocoa lipids synthesis in asexual embryos.

DETAILED DESCRIPTION OF THE INVENTION

Figure 2:
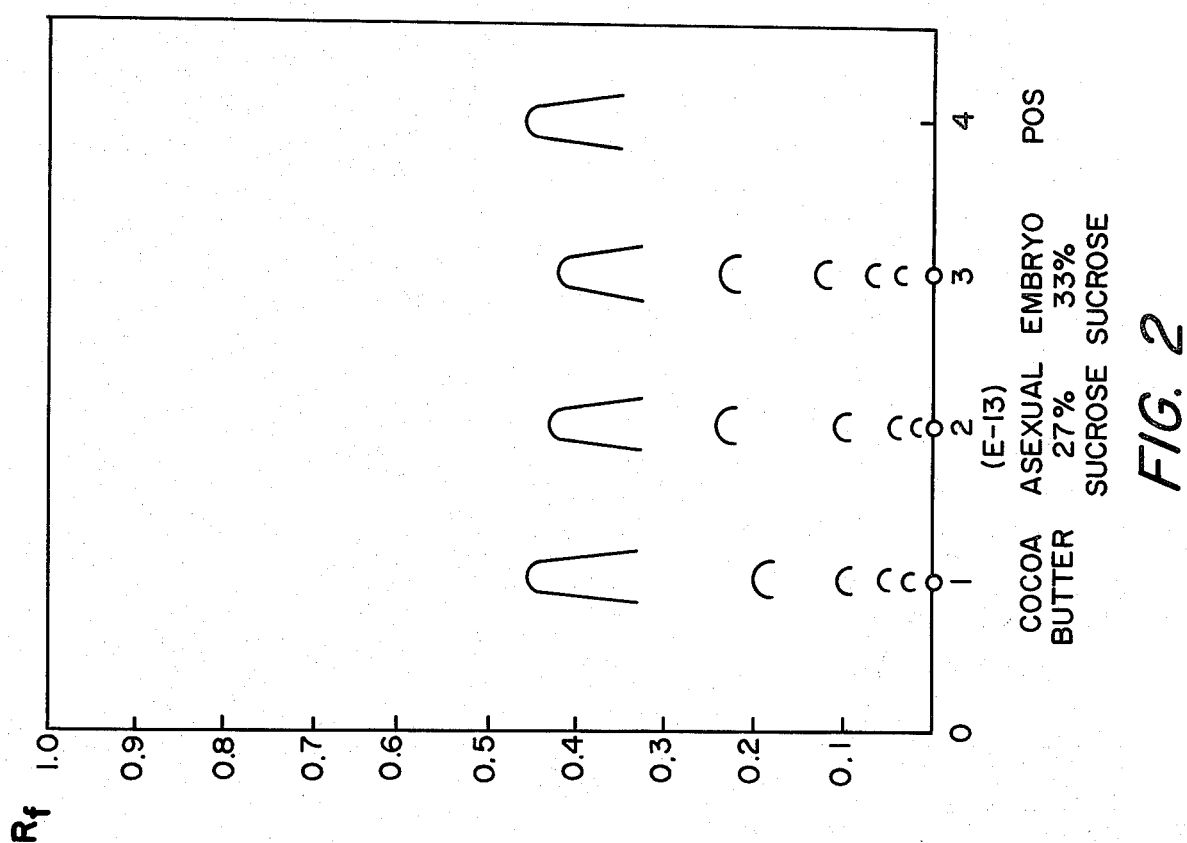
FIG. 2 is a graph showing $R_f$ values of cocoa butter, asexual embryo lipids, and the triglyceride standard oleo-palmitostearin. 57% of cocoa butter is composed of palmitostearin. The plate was pretreated with 12.5% silver nitrate; solvent system was chloroform:benzene:ether (70:30:0.05).

The new process involves media alterations and environmental conditions for the initiation, proliferation, growth and maturation of asexual embryos of cacao in order to produce useful metabolic products from cocoa cotyledons such as cocoa butter and cocoa solids.

The initiation of asexual embryos may start from immature zygotic embryos extracted from developing cocoa pods or from asexual embryos produced from the proliferating embryos as described below. The embryos used as starting material are equivalent to developing embryos found in nature 100 days after pollination and are white in color and about 5–8 mm in length. The zygotic asexual embryos at this stage are placed in a basal medium, as defined in Table 1.

TABLE I

| Cacao Basal Medium | |
|---|---|
| Components | mg/liter |
| Salts[z] | |
| $NH_4NO_3$ | 1650 |
| $KNO_3$ | 1900 |
| $CaCl_2 \cdot 2H_2O$ | 440 |
| $MgSO_4 \cdot 7H_2O$ | 370 |
| $KH_2PO_4$ | 170 |
| Na · EDTA | 373 |
| $FeSO_4 \cdot 7H_2O$ | 27.8 |
| KI | 0.83 |
| $H_3BO_3$ | 6.2 |
| $MnSO_4 \cdot 4H_2O$ | 22.3 |
| $ZnSO_4 \cdot 7H_2O$ | 8.6 |
| $Na_2MoO_4 \cdot 2H_2O$ | 0.25 |
| $CuSO_4 \cdot 5H_2O$ | 0.025 |
| $CaCl_2 \cdot 6H_2O$ | 0.025 |
| Organics | |
| myo-inositol | 100 |
| nicotinic acid | 0.5 |
| pyridoxine HCl | 0.5 |
| thiamine HCl | 0.1 |
| glycine | 2.0 |
| casein hydrolysate | 1000 |

[z]Murashige and Skoog, 1962.

The basal medium described above is supplemented with auxin (either α-naphthaleneacetic acid (NAA) at 0.8–80 μM, or indole-3-acetic acid (IAA) at 0.8–80 μM, or 2,4 dichlorophenoxyacetic acid (2,4-D) at 8.0–80 μM) plus deproteinized coconut water (100 mg/liter) plus a simple sugar such as sucrose (about 30 g/liter) in a semi-solid agar prepared by the addition of 10 g of agar per liter of medium or a liquid medium. In this initiating medium (hereafter referred to as Medium I), over 60% of zygotic embryos initiated asexual embryos as shown in Table 2:

TABLE 2

Interaction between auxin (NAA, IAA and 2,4-D) and coconut water (CW) on asexual embryogenesis in cacao

| | | Embryogenic cultures/total cultures | | | |
|---|---|---|---|---|---|
| Auxin | CW | NAA (8.0 μM) | IAA (8.0 μM) | 2,4-D (8.0 μM) | Total* |
| 0 | 0 | 0/9 | 0/8 | 1/9 | 1/26 (4%) |
| 0 | + | 0/10 | 2/7 | 1/8 | 3/25 (12%) |
| + | 0 | 0/10 | 1/7 | 1/7 | 2/24 (8%) |
| + | + | 3/10 | 7/8 | 5/6 | 15.24 (62%) |

*Percent embryogenic cultures of total culture in parenthesis.

The asexual embryos so initiated in Medium I may be maintained in a proliferating state in the basal medium+sucrose 30 g/liter in solid (10 g agar/liter) or liquid medium but the auxin and coconut water are no longer required. This proliferating medium is referred to as Medium II. Medium II tissues have maintained their embryogenic competence for two years with no evidence of a diminution of embryogenic potential.

Figure 1:
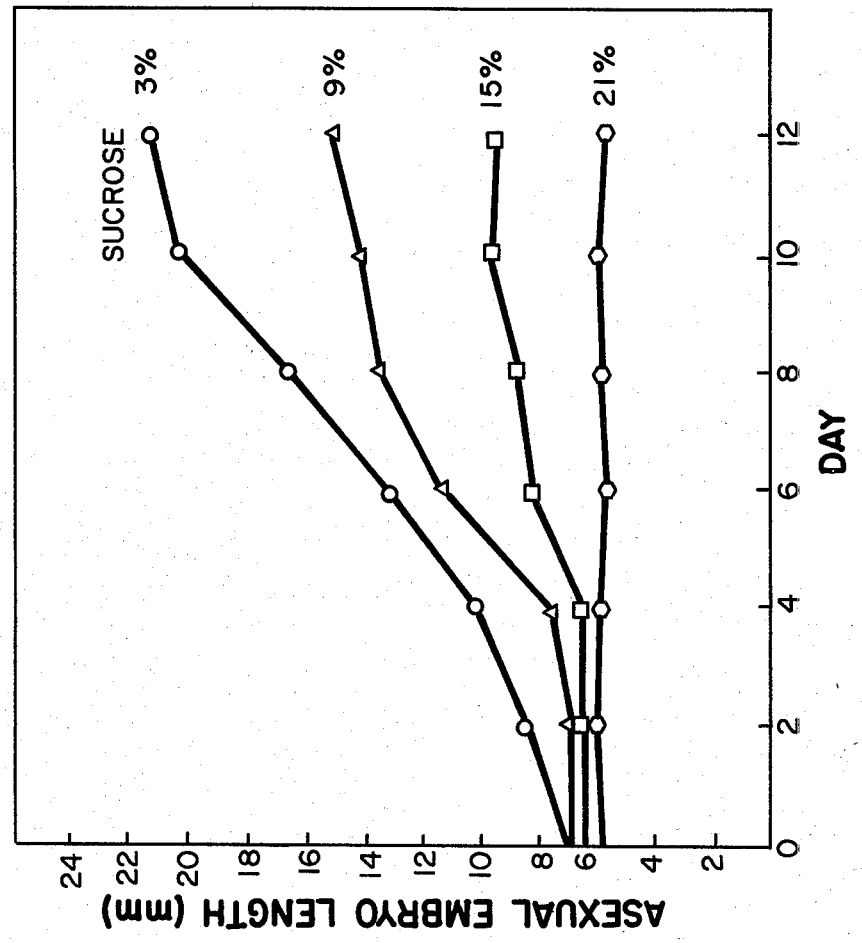
FIG. 1 is a graphic representation showing the increase in asexual embryo length vs. days of growth using the process of this invention.

The growth of asexual embryos produced in Medium II without premature germination is achieved using the basal medium+a sugar such as sucrose or glucose at 15 g/liter to 150 g/liter in a liquid medium. This growth medium is referred to as Medium III. The embryos are washed with Medium III in a rotating culture system or aerated by some other means. Under these conditions, embryo length increases from 7 mm to 20 mm in 12 days as shown in FIG. 1. Growth in this system is inhibited if sucrose levels are more than 30 g/liter to 150 g/liter. Enhancement of growth at this stage may be increased with the addition of deproteinized coconut water at 100 ml/liter.

Upon the asexual embryos reaching at least double their initial length, usually over about 15 mm, they are then stimulated to develop and mature to resemble normal maturing zygotic embryos (i.e., normal cocoa seeds produced in pods by the cocoa tree) by increasing the concentration of sugar, such as sucrose or glucose, and by maintaining cultures either washed with Medium III in a rotating culture system or aerated in some other manner. The sugar concentration is increased in a stepwise manner as in the following Table 3:

TABLE 3

| Sucrose concentration (g/liter) | Days |
|---|---|
| 30 (low sugar) | 10 |
| 90 | 2 |
| 150 | 2 |
| 210 | 2 |
| 270 (high sugar) | up to 44 days |

This maturation media sequence is referred to as Medium IV. These developmental and maturation events include an increase in lipid production, a shift in fatty acid ratios to resemble those found in cocoa butter, and the distribution of triglycerides to resemble the triglyceride pattern of cocoa butter.

The lipids obtained from asexual embryos initiated, proliferated, grown and matured by the outlined procedures above resemble those of commercial cocoa butter when measured by two separate methods, i.e., (1) fatty acid distribution by gas chromatography and (2) triglyceride separation by argentation thin layer chromatography. The fatty acid composition of embryos E-13 and 4-11, which were grown in 270 g/liter sucrose for 20 days and 30 days, respectively, after the appropriate transfers, is similar to commercial cocoa butter as shown in Table 4.

TABLE 4

Fatty acid distribution of asexual embryos E-13 and 4-11, and commercial cocoa butter. Embryos E-13 and 4-11 were grown in high sucrose media for 20 and 30 days, respectively

| | Fatty acid distribution (mole %) | | | | | |
|---|---|---|---|---|---|---|
| | Palmitic acid | Stearic acid | Oleic acid | Linoleic acid | Linolenic acid | Arachidic acid |
| E-13 | 26.6 | 27.6 | 29.8 | 13.8 | 0.9 | 1.3 |
| 4-11 | 27.7 | 35.2 | 28.6 | 6.6 | 0.6 | 1.3 |
| Cocoa butter | 27.7 | 31.3 | 36.8 | 3.8 | 0.3 | 1.0 |

The triglyceride separation of E-13 and cocoa butter is also similar as shown in FIG. 2.

The results of the fatty acid distribution and triglyceride separation show that the lipid development of asexual embryos cultured as described resembles the lipids of normal embryos produced in pods from growing cocoa trees. This shows that asexual embryos grown as described produce desirable metabolic products such as cocoa butter.

What is claimed is:

1. A non-agricultural method for the production of cacao embryos comprising the steps of:
   (A) treatment of immature zygotic cacao embryos in a basal medium in the presence of a growth enhancer to initiate asexual embryos;
   (B) proliferating said embryos by low sugar amendment of said basal media after removal of said growth enhancer;
   (C) growing said embryos in said media under aerated conditions to optimum size under said low sugar conditions;
   (D) continuing the growth of said embryos in said media under aerated conditions and by a high sugar amendment to the said basal media; and
   (E) harvesting the embryos so produced.

2. The method according to claim 1 in which said low sugar amendment is accomplished by addition to the basal media of a solution containing sugar in the range of about 15 g/liter to about 150 g/liter.

3. The method according to claim 2 in which the sugar is selected from a group consisting of sucrose and glucose.

4. The method according to claim 1 in which the embryo optimum size is at least about double the initial length of the embryo.

5. A mature cacao asexual embryo produced according to the method of claim 1.

6. A process for the production of cacao embryos comprising the steps of:
   (A) treatment of asexual embryos in a basal media in the presence of a growth enhancer and by sugar amendment of said media thereby initiating additional asexual embryos;
   (B) proliferating said embryos by low sugar amendment of said basal media after removal of said growth enhancer;
   (C) growing said additional asexual embryos in said media under aerated conditions to optimum size under said low sugar conditions;
   (D) continuing the growth of said additional asexual embryos in said media under aerated conditions in the presence of a high sugar amendment to the said basal media; and
   (E) harvesting the embryos so produced.

7. A mature cacao asexual embryo produced according to the method of claim 6.

8. A non-agricultural method for production of cacao embryos comprising the steps of:
   (A) treatment of immature zygotic cacao embryos in a basal growth media in the presence of a growth enhancer and a solution of sugar having a concentration of between about 1.5% to about 15%;
   (B) proliferation of said embryos in the continued presence of said sugar solution but after the growth enhancer has been substantially removed from said growth media;
   (C) growing said embryos under aerated conditions in the continued presence of said sugar solution until the rate of increase in length of said embryos substantially diminishes;
   (D) continuing the growth of said embryos under said aerated conditions with the concentration of the sugar solution being gradually increased to above about 21%; and
   (E) harvesting the embryos so produced.

9. The method according to claim 8 in which deproteinized coconut water is added at Step (C).

10. The method according to claim 9 in which the said deproteinized coconut water is at a concentration of about 100 ml/liter.

11. The method according to claim 8 in which Step (D) is commenced when said embryo has attained at least about double its initial length.

12. A mature cacao asexual embryo produced according to the method of claim 8.

* * * * *